United States Patent
Wu et al.

(10) Patent No.: US 10,483,004 B2
(45) Date of Patent: Nov. 19, 2019

(54) MODEL-BASED TEETH RECONSTRUCTION

(71) Applicant: Disney Enterprises, Inc., Burbank, CA (US)

(72) Inventors: Chenglei Wu, Pittsburgh, PA (US); Derek Bradley, Zürich (CH); Thabo Beeler, Zürich (CH); Markus Gross, Zürich (CH)

(73) Assignees: DISNEY ENTERPRISES, INC., Burbank, CA (US); ETH ZÜRICH (EIDGENÖSSISCHE TECHNISCHE HOCHSCHULE ZÜRICH), Zürich (CH)

( * ) Notice: Subject to any disclaimer, the term of this patent is extended or adjusted under 35 U.S.C. 154(b) by 0 days.

(21) Appl. No.: 15/280,919

(22) Filed: Sep. 29, 2016

(65) Prior Publication Data
US 2018/0085201 A1    Mar. 29, 2018

(51) Int. Cl.
*G16H 50/50*    (2018.01)
*A61C 13/00*    (2006.01)
*G16H 70/20*    (2018.01)
*G16H 70/60*    (2018.01)
(Continued)

(52) U.S. Cl.
CPC ......... *G16H 50/50* (2018.01); *A61C 13/0004* (2013.01); *G16H 70/20* (2018.01); *G16H 70/60* (2018.01); *A61D 5/00* (2013.01); *G06N 20/00* (2019.01)

(58) Field of Classification Search
None
See application file for complete search history.

(56) References Cited

U.S. PATENT DOCUMENTS

2002/0013684 A1* 1/2002 Toyama ............... G06T 17/00
703/2
2002/0015934 A1* 2/2002 Rubbert ............... A61C 7/00
433/29

(Continued)

OTHER PUBLICATIONS

Abdelmunim et al., "A 3d human teeth database construction based on a point based shape registration", In IEEE ICIP, 2011, 1617-1620.

(Continued)

*Primary Examiner* — Douglas King
(74) *Attorney, Agent, or Firm* — Kilpatrick Townsend & Stockton LLP

(57) ABSTRACT

A system and method for non-invasive reconstruction of an entire object-specific or person-specific teeth row from just a set of photographs of the mouth region of an object (e.g., an animal) or a person (e.g., an actor or a patient) are provided. A teeth statistic model defining individual teeth in a teeth row can be developed. The teeth statistical model can jointly describe shape and pose variations per tooth, and as well as placement of the individual teeth in the teeth row. In some embodiments, the teeth statistic model can be trained using teeth information from 3D scan data of different sample subjects. The 3D scan data can be used to establish a database of teeth of various shapes and poses. Geometry information regarding the individual teeth can be extracted from the 3D scan data. The teeth statistic model can be trained using the geometry information regarding the individual teeth.

16 Claims, 10 Drawing Sheets

(51) Int. Cl.
  *A61D 5/00*     (2006.01)
  *G06N 20/00*    (2019.01)

(56) References Cited

U.S. PATENT DOCUMENTS

| | | | | |
|---|---|---|---|---|
| 2002/0041285 | A1* | 4/2002 | Hunter | G06T 3/0093 |
| | | | | 345/474 |
| 2002/0055800 | A1* | 5/2002 | Nikolskiy | G06F 19/321 |
| | | | | 700/98 |
| 2003/0215764 | A1* | 11/2003 | Kopelman | A61C 7/00 |
| | | | | 433/24 |
| 2006/0063135 | A1* | 3/2006 | Mehl | A61C 13/0004 |
| | | | | 433/223 |
| 2007/0080967 | A1* | 4/2007 | Miller | G06K 9/00208 |
| | | | | 345/473 |
| 2008/0020350 | A1* | 1/2008 | Matov | G06T 17/20 |
| | | | | 433/213 |
| 2013/0107003 | A1* | 5/2013 | Lim | G06T 13/40 |
| | | | | 348/46 |
| 2014/0085293 | A1* | 3/2014 | Konoplev | A63F 13/12 |
| | | | | 345/419 |

OTHER PUBLICATIONS

Alexander et al., "Creating a real-time photoreal digital actor", In ACM SIGGRAPH 2013 Posters, 2013, 1:1-1:1.
Alexander et al., "The digital emily project: Photo-real facial modeling and animation", In ACM SIGGRAPH 2009 Courses, 2009, 2:1-12:15.
Bérard et al., "High-quality capture of eyes", ACM Tran781s. Graphics (Proc. SIGGRAPH Asia) 33, 2014, 223:1-223:12.
Beeler et al., "Coupled 3D Reconstruction of Sparse Facial Hair and Skin", ACM Trans. Graphics, vol. 31, No. 4, Article 117, Jul. 2012, pp. 117:1-117:10.
Beeler et al., "High-quality passive facial performance capture using anchor frames", ACM Trans. Graphics (Proc. SIGGRAPH) 30, 2011, 75:1-75:10.
Beeler et al., "High-quality single-shot capture of facial geometry", ACM Trans. Graphics (Proc. SIGGRAPH), 2010, 40:1-40:9.
Bermano et al., "Detailed spatio-temporal reconstruction of eyelids", ACM Trans. Graphics (Proc. SIGGRAPH) 34, 44:1-44:11.
Blanz et al., "A Morphable Model for the Synthesis of 3D Faces", SIGGRAPH '99, Proceedings of the 26th Annual Conference on Computer Graphics and Interactive Techniques, 1999, 187-194.
Blanz et al., "A statistical method for robust 3d surface reconstruction from sparse data", In 3DPVT, 2007, 293-300.
Buchaillard et al., "3d statistical models for tooth surface reconstruction", Comput. Biol. Med. 37, 2007, 1461-1471.
Cao et al., "Displaced dynamic expression regression for real-time facial tracking and animation", ACM Trans. Graphics (Proc. SIGGRAPH) 33, 2014, 43:1-43:10.
Cao et al., "Real-time high-fidelity facial performance capture", ACM Trans. Graph. 34 (4), 2015, 46:1-46:9.
Carter et al., "Shape from shading for hybrid surfaces as applied to tooth reconstruction", In IEEE ICIP, 2010, 4049-4052.
Dale et al., "Video face replacement", In ACMTrans. Graphics (Proc. SIGGRAPH Asia), vol. 30 2011, 130:1-130:10.
Dempster et al., "Maximum likelihood from incomplete data via the em algorithm", Journal of the Royal Statistical Society 39, 1977, 1-38.
Dollár et al., "Supervised learning of edges and object boundaries", In IEEE CVPR, 2006, 1964-1971.
Echevarria et al., "Capturing and stylizing hair for 3d fabrication", ACM Trans. Graphics (Proc. SIGGRAPH) 33, 2014, 125:1-125:11.
El Munim et al., "Shape representation and registration using vector distance functions", In IEEE CVPR, 2007, 1-8.
Farag et al., "Model-based human teeth shape recovery from a single optical image with unknown illumination", In Medical Computer Vision: Recognition Techniques and Applications in Medical Imaging (MCV '12), 2013, 263-272.
Garrido et al., "Automatic face reenactment", In IEEE CVPR, 2014, 4217-4224.
Garrido et al., "Modifying face video of actors for plausible visual alignment to a dubbed audio track", Comput. Graph. Forum 34, 2015, 193-204.
Garrido et al., "Reconstructing detailed dynamic face geometry from monocular video", ACM Trans. Graphics (Proc. SIGGRAPH Asia) 32, 2013, 158:1-158:10.
Ghosh et al., "Multiview face capture using polarized spherical gradient illumination", ACM Trans. Graphics (Proc. SIGGRAPH Asia) 30, 2011, 129:1-129:10.
Grigorescu et al., "Comparison of texture features based on gabor filters", IEEE Trans.Image Proc. 11, 2002, 1160-1167.
Hewer et al., "A hybrid approach to 3D tongue modeling from vocal tract MRI using unsupervised image segmentation and mesh deformation", In Interspeech, 2014, 418-421.
Hewer et al., "A statistical shape space model of the palate surface trained on 3D MRI scans of the vocal tract", 18th International Congress of Phonetic Sciences (ICPhS), 2015.
Hu, "Single-view hair modeling using a hairstyle database", ACM Trans. Graphics (Proc. SIGGRAPH) 34, 2015.
Ichim et al., "Dynamic 3d avatar creation from hand-held video input", ACM Trans. Graphics (Proc. SIGGRAPH) 34, 2015, 45:1-45:14.
Kawai et al., "Data-driven speech animation synthesis focusing on realistic inside of the mouth", Journal of Information Processing 22, 2014, 401-409.
Kim et al., "A decision tree framework for spatiotemporal sequence prediction", Proceedings of the 21th ACM SIGKDD International Conference on Knowledge Discovery and Data Mining, ACM, 2015, 577-586.
Le et al., "An interactive geometric technique for upper and lower teeth segmentation", Proceedings of the 12th International Conference on Medical Image Computing and Computer-Assisted Intervention: Part II, Springer-Verlag, Berlin, Heidelberg, MICCAI '09, 2009, 968-975.
Mehl, "Biogeneric tooth: a new mathematical representation for tooth morphology in lower first molars", Eur. J. Oral. Sci. 113, 2005, 333-340.
Mehl et al., "New Procedure for Fully Automatic Occlusal Surface Reconstruction by Means of a Biogeneric Tooth Model", Int. J. Comput. Dent. 8, 2005, 13-25.
Mostafa et al., "Statistical morphable model for human teeth restoration", IEEE ICIP, 2014, 4285-4288.
Munim et al., "A new variational approach for 3d shape registration", International Symposium on Biomedical Imaging: From Nano to Macro (ISBI '07), 2007, 1324-1327.
Nagano et al., "Skin microstructure deformation with displacement map convolution", ACM Trans. Graphics (Proc. SIGGRAPH) 34, 2015.
Omachi et al., "Tooth shape reconstruction from ct images using spline curves", Wavelet Analysis and Patter Recognition, vol. 1, 2007, 393-396.
Rousseeuw et al., Robust Regression and Outlier Detection. John Wiley & Sons, Inc., New York, NY, USA., 1987.
Shi et al., "Automatic acquisition of high-fidelity facial performances using monocular videos", ACM Trans. Graphics (Proc. SIGGRAPH Asia) 33, 2014, 222:1-222:13.
Sorkine et al., "Laplacian surface editing", In Proceedings of the EUROGRAPHICS/ACM SIGGRAPH Symposium on Geometry Processing, ACM Press, 2004, 179-188.
Suwajanakorn et al., "Total moving face reconstruction", ECCV, 2014, 796-812.
Suwajanakorn, "What makes tom hanks look like tom hanks", Proc. ICCV, 2015.
Thies et al., "Real-time expression transfer for facial reenactment", ACM Trans. Graphics (Proc. SIGGRAPH Asia) 34, 2015.
Valgaerts et al., "Lightweight binocular facial performance capture under uncontrolled lighting", ACM Trans. Graphics (Proc. SIGGRAPH Asia) 31 (6), 2012.

(56) References Cited

OTHER PUBLICATIONS

Webb et al., "Structure from motion of rigid and jointed objects", Artificial Intelligence 19, 1982, 107-130.
Weyrich et al., "Analysis of human faces using a measurement-based skin reflectance model", ACM SIGGRAPH '06, 2006, 1013-1024.
Yanagisawa et al., "Tooth shape reconstruction from dental ct images with the region-growing method", Dentomaxillofacial Radiology 43, 6, 20140080, 2014.
Zheng et al., "A novel 3d morphing approach for tooth occlusal surface reconstruction", Comput. Aided Des. 43, 2011, 293-302.
Zollhofer et al., "Real-time non-rigid reconstruction using an rgb-d camera", ACM Transactions on Graphics (TOG) 33, 2014, 156.

* cited by examiner

MODEL-BASED TEETH RECONSTRUCTION

BACKGROUND OF THE INVENTION

Digital models have become widely used in many fields, from digital animation to remote medical diagnosis. Over the past decades, both research and industry have made tremendous progress when it comes to the creation of digital faces, mostly focusing on appearance, shape, and deformation of skin. More recently, some work has emerged which also targets other facial features, such as the eyes and facial hair. However, capturing the mouth cavity in general, and teeth in particular, has only received very little attention so far. Teeth contribute substantially to the appearance of a face, and expressions may convey a very different intent if teeth are not explicitly modeled. Furthermore, teeth can be an invaluable cue for rigid head pose estimation and are essential for physical simulation, where they serve as a collision boundary. In addition, in medical dentistry, digital teeth models have long become a central asset, since they allow to virtually plan a patient's dental procedure.

Many efforts to capture teeth have stemmed from the medical dental field. While plaster-cast imprints are widely in the past in dental clinics, more and more intra-oral scanners are making their way into the clinics. While these devices can capture the shape of the teeth at high quality, the capture procedure is very invasive and the devices themselves can be costly and may not be readily available. Moreover, although methods using these devices can yield high-quality models, they are time consuming, expensive, and may impose health risks especially when used frequently.

Systems such as photogrammetric camera rigs, which are not very invasive and have become the de-facto standard for facial capture, have so far not been able to faithfully reconstruct the teeth at high quality. This is mainly due to the complex appearance properties of teeth. Teeth are both extremely specular due to the translucent enamel coating and highly diffuse due to the underlying dentine, which exhibits strong subsurface scattering. Consequently, teeth have only few visible features, the strongest being the boundary between individual teeth, which however is not a feature on the surface, thus reconstructing teeth using photogrammetric approaches is very challenging. Some conventional methods have tried exploiting reflectance properties of teeth by using variants of shape-from-shading. However, these methods are still challenged by occlusions and often capture incomplete medium-quality models of a single tooth or the occlusal (i.e. biting) surface.

Camera-based reconstruction of the mouth interior is further complicated by non-trivial occlusions. It is often hard for people to open the mouth sufficiently wide without the use of dedicated lip spreading devices, and even then the entire mouth cavity is typically not visible from a single pose. Up to now, there is no passive photogrammetric approach for reconstructing detailed actor-specific teeth rows, and in most practical animation settings, the mouth interior is modeled by artists in a tedious manual process. Some conventional methods resort to image-based retrieval strategies to resynthesize the mouth from similar video frames or a dedicated image-database. However, these methods often tend to lead to ghosting and temporal aliasing effects. Some other conventional methods use non-person specific teeth row models to reconstruct 3D model's teeth. While those methods yield plausible re-rendering results, but the true person-specific mouth appearance, in particular under extreme facial expressions, is not reproduced under those methods.

BRIEF SUMMARY OF THE INVENTION

Embodiments can enable non-invasive reconstruction of an entire object-specific or person-specific teeth row from just a set of photographs of the mouth region of an object (e.g., an animal) or a person (e.g., an actor or a patient), respectively. A teeth statistic model defining individual teeth in a teeth row can be developed for achieving this. Under this model-based approach, a personalized high-quality 3D teeth model can be reconstructed using just a sparse set of (e.g., uncalibrated) images or a short monocular video sequence as input. The teeth statistic model can be employed to reconstruct a 3D model of teeth based on images of teeth of an object or a person corresponding to the 3D model. In some embodiments, the teeth statistic model can jointly describe shape and pose variations per tooth, and as well as placement of the individual teeth in the teeth row. Unlike related approaches in the medical field, the model-based approach in accordance with the disclosure is non-invasive and can be used to reconstruct a geometric model of the entire teeth row including the gums from images captured from afar and potentially simultaneously. Under this approach, statistical information of a novel parametric tooth prior learned from high-quality 3D dental scans that models the global deformations of an entire teeth row as well as the individual variation of each single tooth can be used to fit teeth information acquired from the images. The model-based approach in accordance with the disclosure brings 3D teeth reconstruction within reach of commodity use, without requiring expensive specialized equipment. This versatile and easy-to-use approach can be useful in medical dentistry as well as in the entertainment industry, where captured teeth and gum model can be seamlessly integrated into existing photogrammetric multi-camera setups for face capture.

In various embodiments, for developing the teeth statistic model that can be used to reconstruct the 3D model's teeth, 3D scan data of teeth rows of different sample subjects can be obtained. The 3D scan data can be used to establish a database of teeth of various shapes and poses. Geometry information regarding the individual teeth can be extracted from the 3D scan data. The teeth statistic model can be trained using the geometry information regarding the individual teeth.

The teeth statistic model can be used to reconstruct a 3D model's teeth during a model fitting stage. During that stage, a single image or multiple images of an object's or a person's teeth can be received. Object-specific or person-specific teeth information can then be acquired from the image(s). Such teeth information may include data terms indicating color, edges, shape, maxilla and/or mandible bones and/or any other aspects of the teeth of the object or the person. Parameters of each tooth for the 3D model, corresponding to the object or the person, can be estimated from the statistic model using the teeth information. The teeth parameters can then be used to model the teeth of the 3D model using pre-authored 3D teeth templates.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION OF THE INVENTION

Embodiments are directed to reconstructing a 3D model of teeth using one or more images of a mouth region of an object (e.g., an animal) or a person (e.g., an actor or a patient) corresponding to the 3D model. In some examples in accordance with the disclosure, a realistic 3D teeth model can be reconstructed using as few as a single image of the mouth region of the object or the person. For achieving this, in accordance with the disclosure, a teeth statistic model can be defined and developed. The teeth statistic model can represent shape and pose variation of individual teeth in a teeth row. The teeth statistic model can be used to fit 3D teeth templates to the 3D model by estimating parameters from the one or more images of the mouth region of the object or person corresponding to the 3D model.

One key insight provided by the present disclosure is generalizing tooth shapes for the object or the person using the teeth statistical model. In accordance with the disclosure, the teeth statistic model can encode a local shape variation of each individual tooth, a pose variation of each tooth within a row of teeth, the global position and scale of a row of the teeth, and/or any other aspects regarding the teeth of the object or the person. In certain embodiments, a statistic model is defined and developed for each tooth of a human—i.e., 32 statistical per-tooth models for each of the 32 human teeth are defined and developed. In certain embodiments, statistic teeth row models for relative placement of the teeth are defined and developed. In certain embodiments, the per-tooth model and teeth row model are combined in one statistic teeth model to capture the shape and pose variation of each teeth and as well as the placement each teeth in a teeth row.

Taking human as an example, there are typically 32 individual teeth (28 if the wisdom teeth are removed) for a person, which are separated into two rows (top and bottom) with symmetry. In some embodiments, using this symmetry property of human teeth, 16 per-tooth models can be defined and developed such that each per-tooth model represent human teeth at the same position matching each other at the bottom and top rows. The human teeth can be further divided into basic types—for example, incisor, canine, premolar, and molar. In some embodiments, teeth statistic models can be defined and developed for each of such tooth types.

Figure 1:
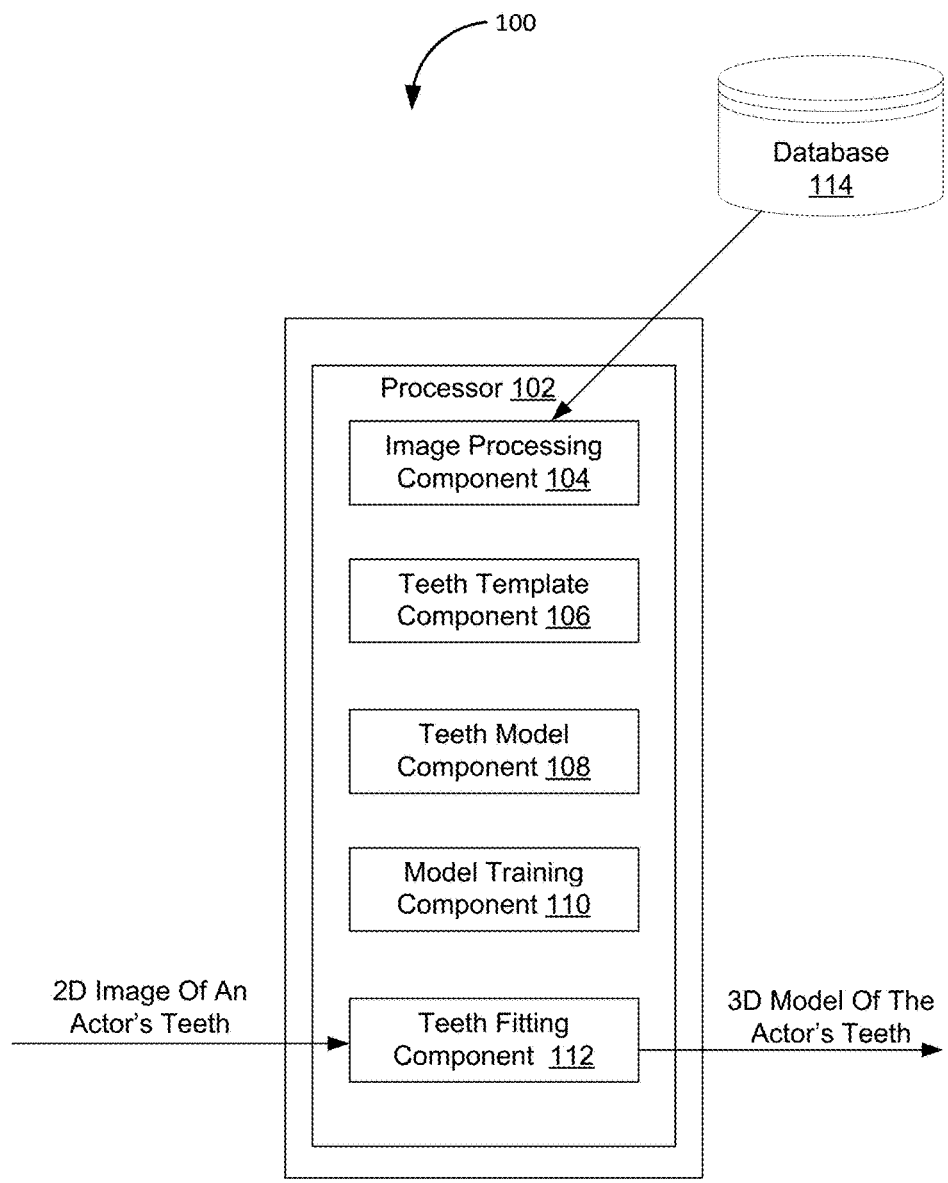
FIG. 1 illustrates generally a computer system for reconstructing a 3D model of teeth by defining and developing a teeth statistic model in accordance with the disclosure.

FIG. 1 illustrates generally a computer system 100 for reconstructing a 3D model of teeth by defining and developing a teeth statistic model in accordance with the disclosure. As shown, system 100 can include one or more of a processor 102 configured to implement computer program components, which can include an image processing component 104, a teeth template component 106, a teeth model component 108, a model training component 110, a teeth fitting component 112, and/or any other components.

The image processing component 104 can be configured to extract and process data from images of teeth rows of different sample subjects, and to obtain geometry information for individual teeth the sample subjects. In some implementations, the image processing component 104 may be configured to receive the images of the teeth rows of the different sample subjects from a database, such as database 114 as shown. In some implementations, the image processing component 104 may be configured to receive, from a user, information indicating segmentation between the teeth and gum for a particular image of a teeth row of a sample subject. In some implementations, the image processing component 104 may be configured to receive, from a user information indicating segmentation between the teeth for the particular image of the teeth row of the sample subject. In those implementations, the image processing component 104 may be configured to automatically segment individual teeth in the particular image using the aforementioned segmentation information.

The teeth template component 106 can be configured to obtain pre-authored teeth templates for fitting the teeth of the sample subjects using the geometry information for the teeth of the sample object obtained by the image processing component 104. In some examples, the pre-authored teeth templates may include artistically created tooth template meshes. In those examples, the teeth template component 106 can be configured to fit instances of the teeth template meshes to individual teeth in the images processed by the image processing component 104. This may involve rigidly aligning to the teeth in the images to the appropriate teeth template mesh and non-rigidly deforming to tightly fit the segmented tooth region using iterative Laplaican deformation, for example as described by Sorkine et al. 2004, which is incorporated by reference herein in its entirety. In some implementations, the teeth template component 106 can be configured to compute a mask indicating which part of the template corresponds to the segmented tooth, and mark the line of vertices corresponding to the gum boundary on the aligned template.

The teeth model component 108 can be configured to retrieve one or more teeth statistic models that can generally encode differences of individual teeth across the subjects. The differences of a given tooth can include variations regarding shape, pose, placement in a teeth row, and/or any other teeth aspects. In some implementations, the teeth statistical model retrieved by the teeth model component 108 can be pre-defined by a user, e.g., a modeler. In some examples, the teeth statistical model retrieved by teeth model component 108 can encode deviation in shape and pose from a canonical teeth row, which can be computed as a mean of the teeth meshes marked by the teeth template component 106. In some implementations, the teeth statistical model retrieved by teeth model component 108 can include 32 human tooth statistical models. In those implementations, each individual tooth statistical model can include parameters that represent average shape of the tooth across the subjects, average pose across the subjects, shape variation of the tooth, relative pose variation of the tooth, rigid transformation that affects the tooth placement in the teeth row, a scaling factor, and/or any other parameters.

The model training component 110 can be configured to train the teeth statistic models retrieved by the teeth model component 108. The training by the model training component 110 may involve evaluating the teeth statistics model(s) retrieved by the teeth model component 108 for a set of teeth to provide an instance of a teeth row that represents either the upper or lower teeth for an individual. In some implementations, the model training component 110 may be configured to align the teeth rows of the subjects as obtained by the teeth template component 106 and the image processing component 104. In those implementations, the model training component 110 can be further configured to compute a mean teeth row by averaging the corresponding vertices of every sample. Based on mean teeth row, the model training component 110 can be configured to compute global rigid transformations and anisotropic scale. For an individual tooth, canonical tooth transformations can be computed based on the mean teeth row. In some examples, the model training component 110 can be configured to perform subspace analysis to determine mean tooth shape for each individual tooth.

The teeth fitting component 112 can be configured to fit the statistical teeth model(s) to teeth information derived from one or more images of a mouth region of an object or a person corresponding to a 3D model. This may involve automatic teeth boundary extraction, estimating the teeth statistic model parameters from the boundaries, recovering teeth color textures from the one or more images to incorporate 3D gums for visualization and/or any operations.

Figure 2:
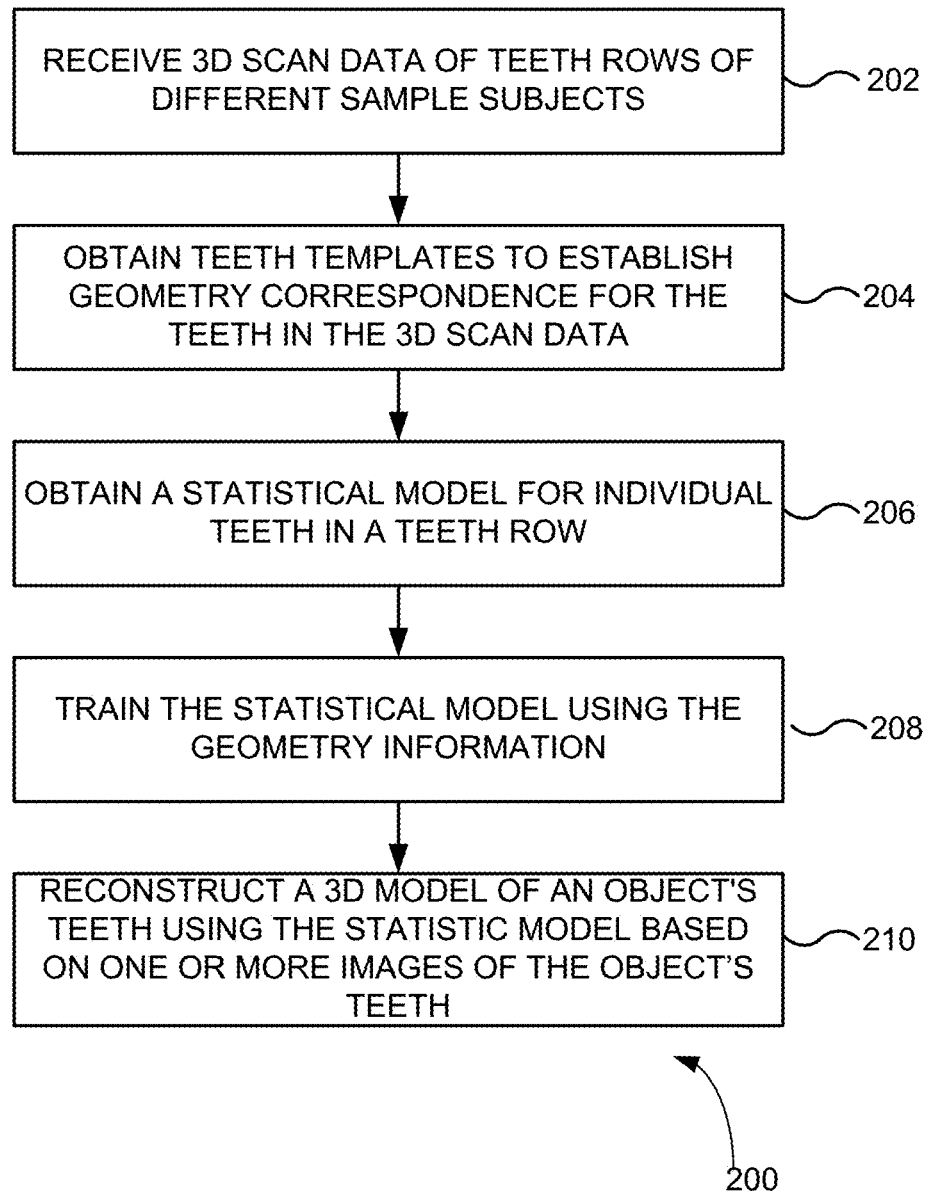
FIG. 2 illustrates an exemplary method for reconstructing a 3D model of teeth using teeth statistic models in accordance with the disclosure.

With the general system architecture for reconstructing a 3D model of teeth using teeth statistic models having been described in FIG. 1, attention is now directed to FIG. 2. FIG. 2 illustrates an exemplary method 200 for reconstructing a 3D model of teeth using teeth statistic models in accordance with the disclosure. The method presented in FIG. 2 and described below is intended to be illustrative and non-limiting. The particular series of processing steps depicted in FIG. 2 is not intended to be limiting. It is appreciated that the processing steps may be performed in an order different from that depicted in FIG. 2 and that not all the steps depicted in FIG. 2 need be performed. In certain implementations, the method 200 may be implemented by a computer system, such as the computer system 100 shown in FIG. 1.

In some embodiments, the method depicted in method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

Figure 4:
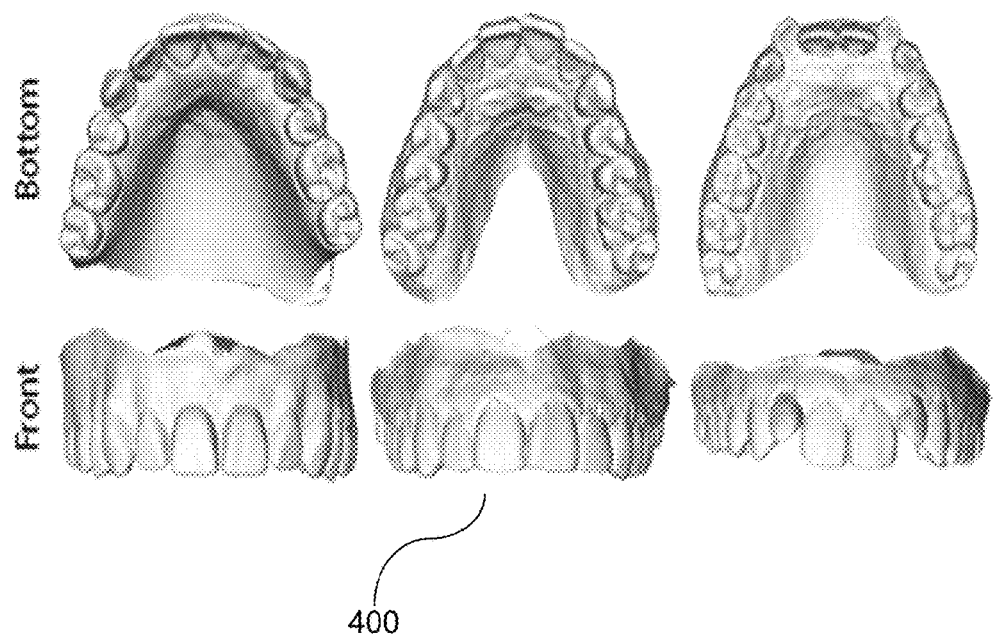
FIG. 4 illustrates three example 3D scans of teeth of human subjects.

At 202, one or more 3D scan data of teeth rows of different subjects can be received. In some implementations, the images received at 202 may include high resolution plaster cast 3D scans of different teeth rows that can be acquired by dentistry scanning devices. FIG. 4 illustrates one example 3D scan 400 of teeth of a human subject can be obtained. In one implementation, 3D scan data of 86 different teeth rows are received with a mixture of upper and lower teeth. However, this is merely illustrative. It should be understood the number of 3D scan data of teeth row that can be received at 202 for training the teeth statistic model(s) may be however desired depending on the situation. For example, in certain situations, less 3D scan data of teeth rows of less subjects may be received if the details of teeth statisic model is not require to be high, while in some other situations, more 3D scan data of teeth rows of more subjects may be received if the details of the teeth statistic model is desired to be high. In some implementations, operations involved in 202 may be implemented by a image processing component similar to the image processing component 104 described and illustrated herein.

It should be noted while the 3D scan data received at 202 can contain detailed tooth geometry information, they can also typically contain imagery of the gums surrounding the teeth and the teeth shown in those images may not in correspondence across the subjects. Furthermore, there may not be semantics for separating the teeth from the gums and/or separating the teeth from each just based on the images. For example, as shown in FIG. 4, the 3D scan 400 of the teeth rows themselves may not have sufficient information for establishing geometry correspondence for individual teeth across different subjects.

Figure 3:
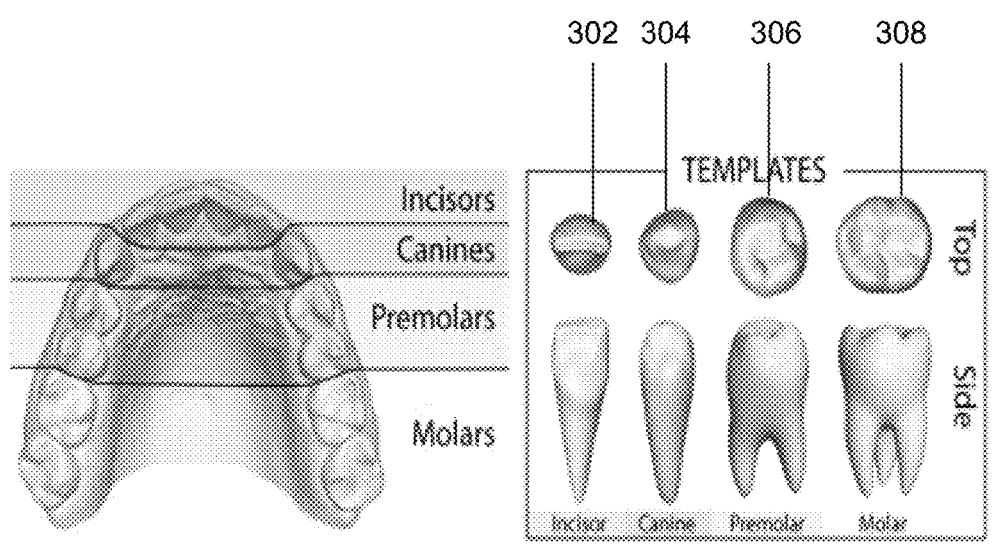
FIG. 3 illustrates four teeth templates can be created for four types of human teeth.

At 204, teeth templates may be received to establish geometry correspondence for the teeth shown in the 3D scan data received at 202. The teeth templates received at 204 can be artistically created, for example as teeth template meshes. In some embodiments, a tooth template is created for each tooth in a teeth row. For example, 32 teeth templates can be created to represent the 32 teeth of a human. In some embodiments, a tooth template is created for each type of teeth. For example, FIG. 3 illustrates four teeth templates can be created for four types of human teeth. As shown in FIG. 3, an incisor template 302, a canine template 304, a premolar template 306, and a molar template 308 can be created to represent the four corresponding types of human teeth.

Figure 5:
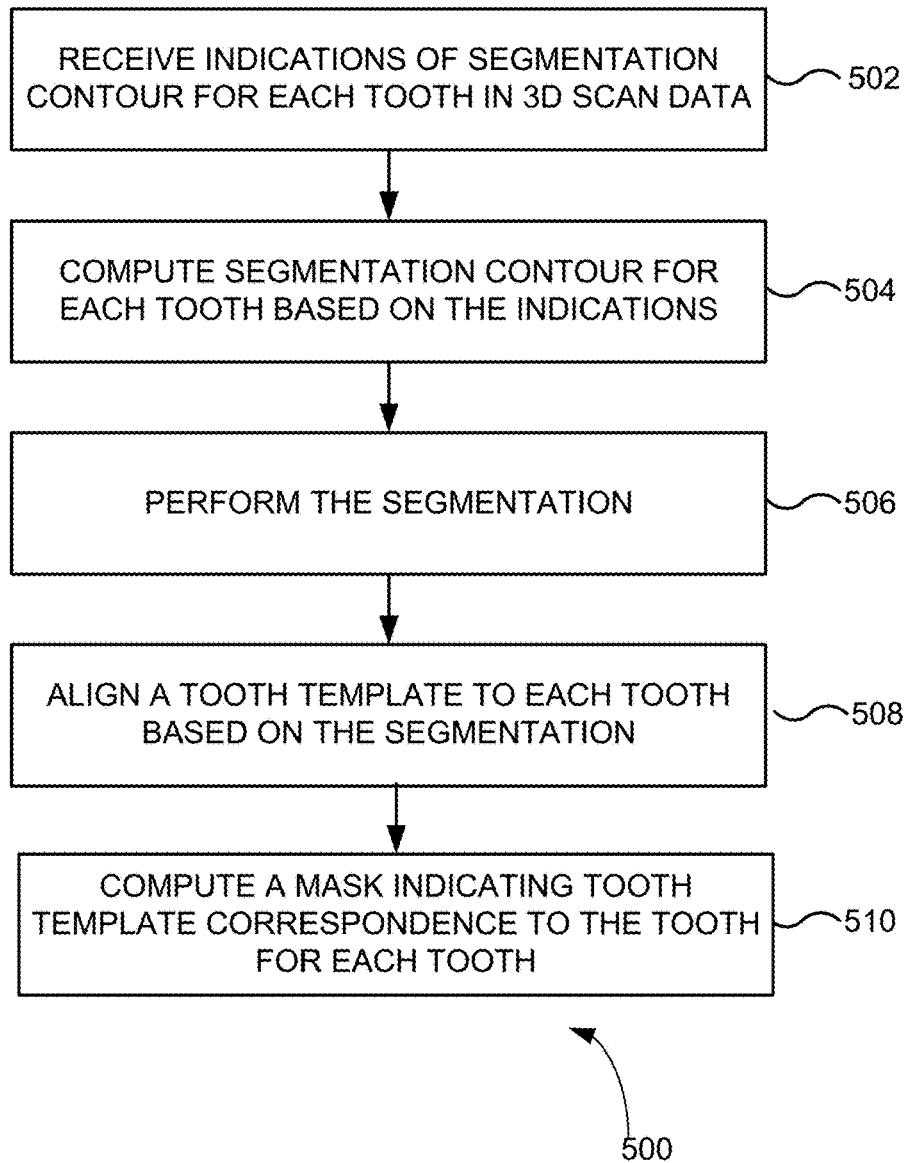
FIG. 5 illustrates on example of semi-automatic template fitting of the teeth templates to the teeth in the 3D scan data for obtaining training data to train a teeth statistical model.

In some embodiments, operations involved in 204 may include fitting the teeth templates to the individual teeth in the 3D scan data received at 202. This can solve the aforementioned segmentation problem and place the teeth in vertex correspondence across the subjects. In some implementations, a semi-automatic template fitting approach can be employed to fit the teeth templates to the teeth in the 3D scan data. FIG. 5 illustrates one example of such an approach. In any case, operations involved in 204 can establish a tooth database of teeth rows with per-tooth mesh correspondence. That is, at 204, a given tooth in a given 3D scan received at 202 can be geometrically mapped to other teeth in other 3D scan data received at 202. In some implementations, operations involved in 204 may be implemented by a teeth template component similar to the teeth template component 106 described and illustrated herein.

Figure 7:
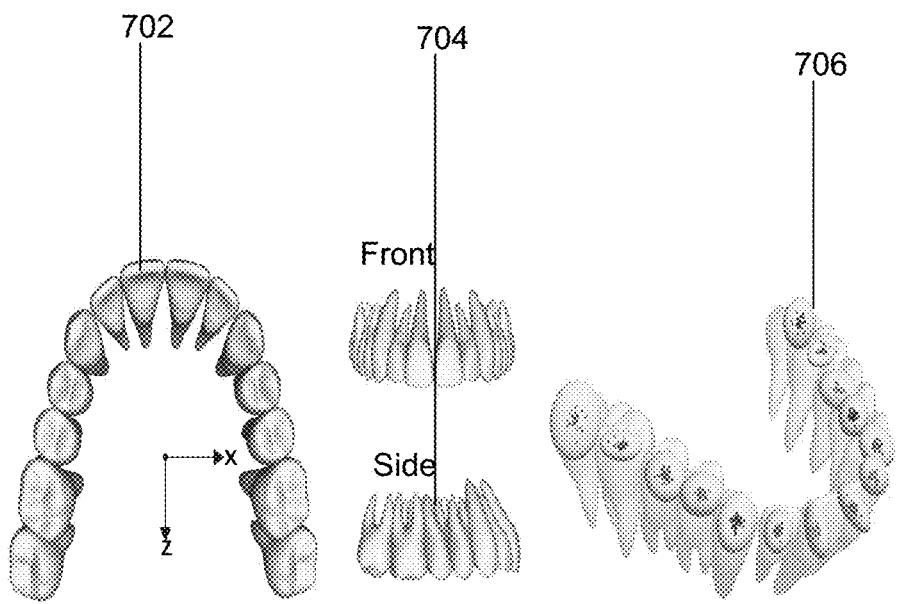
FIG. 7 illustrates an example of a canonical teeth row, and the per-tooth positional variation in the statistical model.

At 206, a statistic model may be obtained for each tooth in a teeth row of the object. For example, a statistic model for each tooth in a teeth row of a human may be obtained from an animator via an interface or may be provided during a configuration stage of system 100. As described above, the statistic model for a given tooth obtained at 206 may account for variations of local shape and arrangements of the given tooth. In some embodiments, the statistic model may encode the deviation in shape and pose from a canonical teeth row, which is computed as the mean of the tooth databased established at 204 in those embodiments. FIG. 7 illustrates an example of such a canonical teeth row. As shown in FIG. 7, the canonical teeth row 702 can be computed as a mean of the tooth database established at 204. The samples 706 of the tooth database can be aligned globally to the canonical teeth row 702 to allow for qualifying the remaining local pose variations 706. The dots shown in 706 correspond to the center of the aligned database samples. As shown, the large ellipse can visualize the computed Gaussian prior distribution at 2a.

In some embodiments, for every tooth τ, canonical parameters for the statistical model for the tooth can include an average shape per tooth $S_\tau^C$ as well as an average pose of tooth $T_\tau^C$. In some embodiments, the statistical model for the tooth may further include a shape-subspace Bτ per tooth that encodes the tooth's variation in shape. Values for these properties in the statistical model can be extracted from the teeth database established at 204 and can remain invariant during image-based tooth fitting later on. In this way, degrees of freedom during the image-based fitting can be parameterized by the shape coefficient $a_\tau$ as well as a rigid transformation matrix Tτ that encodes the relative pose variation per tooth. In some embodiments, global parameters that affect the teeth row as a whole, namely a rigid transformation T as well as anisotropic scaling along all axes Φ, can also be included in the statistical model for the tooth. In one implementation, a specific statistical model for each individual tooth in the teeth row is defined as follows:

$$Z_\tau = T\Phi T_\tau T_\tau^C \left( S_\tau^c + \sum_i^{|B_\tau|} a_\tau^i B_\tau^i \right), \quad (1)$$

where Zτ is the final shape and pose reconstruction of a synthesized tooth in the row, under the model parameters {T, Φ, Tτ, aτ} as described above. In some implementations, operations involved in 206 may be implemented by teeth model component similar to teeth model component 108 described and illustrated herein.

At 208, the statistic model for the individual teeth obtained at 206 can be trained using geometry information for the teeth of the sample subjects obtained at 204. In some embodiments, operations involved in 208 may include evaluating the statistical model as defined in equation 1 above for a set of teeth. In those embodiments, the evaluation can provide an instance of a teeth row that represents either the upper or lower teeth for an object or a person. The training performed at 208 can produce plausible reconstruction of teeth.

In equation 1 described above, the teeth row statistical model is defined by global parameters T and Φ, and as well as the canonical positions $T_\tau^C$. In some embodiments, for training the teeth row statistical model, operations involved in 208 can include aligning the teeth rows in the database established at 204, for example rigidly with anisotropic scale. In implementations, for aligning the teeth rows in the database, one teeth row in the database can be selected as a reference teeth row and other teeth rows in the database can be aligned to the selected teeth row by computing rigid transformations and anisotropic scales. Once aligned, a mean teeth row can be computed by averaging the corresponding vertices of every teeth row. In one implementation, a coordinate system of the mean teeth row is defined by placing the origin between the two frontmost incisors as follows: setting the y-axis to point in the direction from the teeth roots to the crowns, the z-axis to point towards the mouth cavity, and the x-axis to form a right-hand coordinate system with the other axes.

In some embodiments, operations involved in 208 may include computing global rigid transformations and anisotropic scale to align some or all sample teeth rows in the database to the mean teeth row. Since the anisotropic scale, unlike the rigid transformation that accounts for global pose, is due to anatomical differences in the population, the variations in the anisotropic scale may be quantified such that it can be employed as a prior during the image-based fitting later on. In one implementation, the prior on global anisotropic scale is modeled by a multivariate Gaussian distribution $N_\Phi$ over the three degrees of freedom.

In some embodiments, operations involved in 208 may include rigidly aligning corresponding teeth templates obtained at 204 to the individual teeth in the mean teeth row to obtain the canonical tooth transformations $T_\tau^C$. In those embodiments, the corresponding tooth samples of the aligned teeth rows can then be expressed in the local coordinate frame $T_\tau^C$ of the tooth. A pose variation within this local coordinate frame can represent the remaining pose residual for this tooth type, which can be quantified mathematically and can be employed as a prior in the image-based fitting later on. In one implementation, a multivariate Gaussian distribution $N_{T\tau}$ over the six degrees of freedom of the local transformation (three for translation and three for rotation) is constructed, assuming a normal distribution of the samples and a dependency of the individual variables in the rigid transformation. It is noted that, a separate Gaussian distribution for the local transformation of each tooth can be learned. In those embodiments, operations involved in 208 may further include removing the local rigid transformations and aligning all samples of a tooth class, such that the only residual left is due to shape variation, which can be captured in a local shape model described below.

In some embodiments, operations involved in 208 may include subspace analysis to capture shape variations of the individual teeth. In one implementation, a Principal Component Analysis (PCA) is performed to determine an optimal subspace for the individual teeth, assuming the samples follow a normal distribution. PCA can provide a mean tooth shape, represented in our model as the canonical shape per tooth $S_\tau^C$ as well as an orthogonal shape basis $B_T$. In that implementation, for avoiding fitting, the orthogonal shape basis $B_T$ can be truncated to include 95 percent of the energy, which is approximately 4 components for incisors, 6 for canines, and 10 for both premolars and molars, on average. For each tooth, the ring of vertices corresponding to the average gum line observed in the scan data obtained 202 can also be marked.

Figure 8:
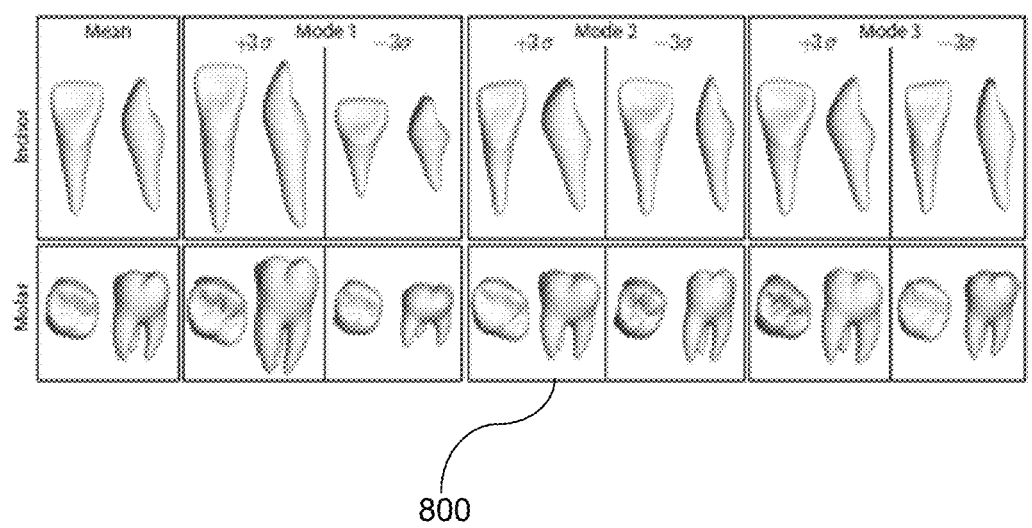
FIG. 8 illustrates some examples of major modes in shape subspaces for an incisor and a molar tooth.

FIG. 8 illustrates some examples of major modes 800 in shape subspaces for an incisor and a molar tooth. In FIG. 8, the modes are displayed at ±3σ. The first two modes (mode 1 and mode 2 as shown) roughly correspond between all teeth, with the first mode corresponding to length, and the second roughly to overall thickness. Higher modes account for tooth specific shape details, e.g. how pronounced the crown is in the case of a molar. As can be seen in FIG. 8, the two major eigenmodes are consistent across teeth. The first one intuitively encodes variation in tooth length, whereas the second one captures thickness changes. Higher modes capture smaller shape changes such as local asymmetries, which differ between different teeth classes. The computed eigenvalues define a zero-mean normal distribution $N_{\sigma\tau}$ for each shape parameter.

In some embodiments, operations involved in 208 can include fitting the shape model to the individual teeth so to replace the teeth the mean teeth row with the canonical shape $\{S_\tau^C\}$, leading to the canonical teeth row statistical model 702 as shown in FIG. 7. The resulting teeth prior is a parametric model that defines the position and shape of a row of teeth with both global and local control. In addition, it provides a trained statistical prior on the variation of model parameters based on a database of scan data obtained at 202, for example high-quality dentistry scans. In some implementations, operations involved in 208 may be implemented by a model training component the same as or substantially similar to the model training component 110 described and illustrated herein.

At 210, a 3D model of teeth can be reconstructed using the statistical models defined and trained as described above based on one or more images of an individual's teeth (e.g., an object or a person's teeth). At 210, geometry information regarding the individual's teeth can be obtained from the one or more images and can be used to fit the per-tooth and teeth row statistical models described above to reconstruct the teeth of the 3D model corresponding to the individual. Operations involved in 210 may include fitting the teeth row and per tooth statistical models jointly based on the image(s) of the individual's teeth. In some embodiments, as few as a single image of teeth data can be used to reconstruct the teeth of the 3D model using the statistical models.

In some implementations, the image-based fitting at 210 may involve a continuous optimization in parameter space for the statistical models, with data terms from color, edges, shapes, maxilla and mandible bones, and/or any other data terms regarding the individual teeth. In some implementations, an initialization is performed from a coarse fit using a generic-detector, for example dlib. The image-based fitting at 210 can extrapolate invisible teeth. In some embodiments, the image-based fitting ensures physical conditions, such as occlusion (upper teeth should match lower teeth) or intersection (teeth should not intersect). In some embodiments, operations involved in 210 may include a clean-up step that improves an appearance of reconstructed teeth after an initial fitting. In some embodiments, operations involved in 210 may further include refining the geometry (for example, exact fit to multi-silhouettes, shape-from-specularity) of the reconstructed teeth. In some implementations, high resolution details are carried over samples from the database established at 204. In those implementations, the closest sample(s) to the fit parameters are retrieved and the details are carried over.

In some implementations, operations involved in 210 may include adding appearance information to the reconstructed teeth. For example, a regression model that maps from a frontal picture of the teeth to appearance values can be trained and learned. For training the regression model, the aforementioned shape training at 208 can be used to get geometry of the teeth, and to capture the teeth with a ringflash (and maybe also sideflashes, temporarily multiplexed), with a retroreflector behind the teeth. It is contemplated that such training may be performed with or without the ringflash and/or the retroreflector. Since light coming from the flash, travelling through the teeth, and hitting the retroreflector will take the exact path back, translucent material (often at the tip of the frontal teeth) will appear brighter when captured with retroreflector, straight on. From this, translucency of the teeth can be estimated. It is contemplated that polarization may also be used to determine an appearance of the teeth. For example, a behavior of the polarized light traveling through the teeth can be determined and determine whether the translucent part of the teeth change the polarization much. If not, a retroreflector can be used to capture the light that has a polarized coating, since cross-polarized light from the flash would not be retro-reflected but parallel polarized light would be. In some embodiments, polarized filters in front of the lens can be used to extract specularities.

In some implementations, operations involved in 210 can be implemented using a teeth fitting component the same or substantially similar to the teeth fitting component 112 described and illustrated herein FIG. 5 illustrates on example of semi-automatic template fitting of the teeth templates to the teeth in the 3D scan data for obtain training data to train the teeth statistical models described above. The method presented in FIG. 5 and described below is intended to be illustrative and non-limiting. The particular series of processing steps depicted in FIG. 5 is not intended to be limiting. It is appreciated that the processing steps may be performed in an order different from that depicted in FIG. 5 and that not all the steps depicted in FIG. 5 need be performed. In certain implementations, the method 500 may be implemented by a computer system, such as the computer system 1000 shown in FIG. 10.

In some embodiments, the method depicted in method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

Figure 6:
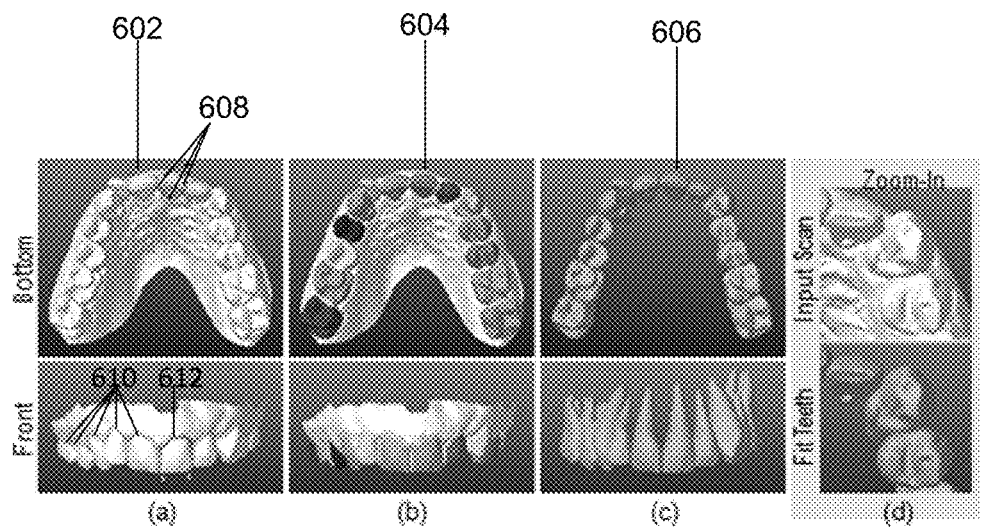
FIG. 6 illustrates an example of teeth contour segmentation and teeth template fitting based on the teeth contour segmentation.

At 502, indications of segmentation contours for individual teeth in a 3D scan can be received. For example, a user may be provided a graphical user interface to define the segmentation contour for each tooth by clicking a few points at the inter-tooth boundaries and the boundaries between teeth and gums in the scan. This is illustrated in FIG. 6. Image 602, where the contour for the left incisor 612 is highlighted in purple and the other contours 610 are shown in green. In addition, the user can be enabled to select a few predefined landmarks per tooth (three for incisors and canines, and five for premolars and molars), which will guide the registration and seed the segmentation. In FIG. 6, image 602 shows the landmarks 608 for one of the incisors in red.

At 504, segmentation contour for each contour can be computed based on the indications received at 502. For example, the segmentation contours can be computed automatically by following high curvature paths between the points highlighted by the user.

At 506, segmentation can be performed. For example, segmentation can be performed by flood-filling from the selected landmarks until the segmentation contours are reached. In FIG. 6, image 604 illustrates this.

At 508, a tooth template can be aligned to each tooth based on the segmentation. Operations involved in 508 may include, for each tooth, rigidly aligning the appropriate template mesh to the tooth given the selected landmarks, and then non-rigidly deforming to tightly fit the segmented tooth region using iterative Laplacian deformation, as described by Sorkine et al. 2004, which is incorporated by reference in its entirety herein, with soft vertex constraints computed as the closest surface point along the normal direction in each iteration. In FIG. 6, image 606 illustrates this.

At 510, a mask indicating tooth template correspondence to the tooth can be computed for each tooth. For example, the mask indicating which part of the template corresponds to the segmented tooth can be computed, and also the line of vertices corresponding to the gum boundary on the aligned template can be marked. Since the remainder of the template has just been deformed as rigidly as possible, it can also be considered when computing the teeth statistical model.

Figure 9:
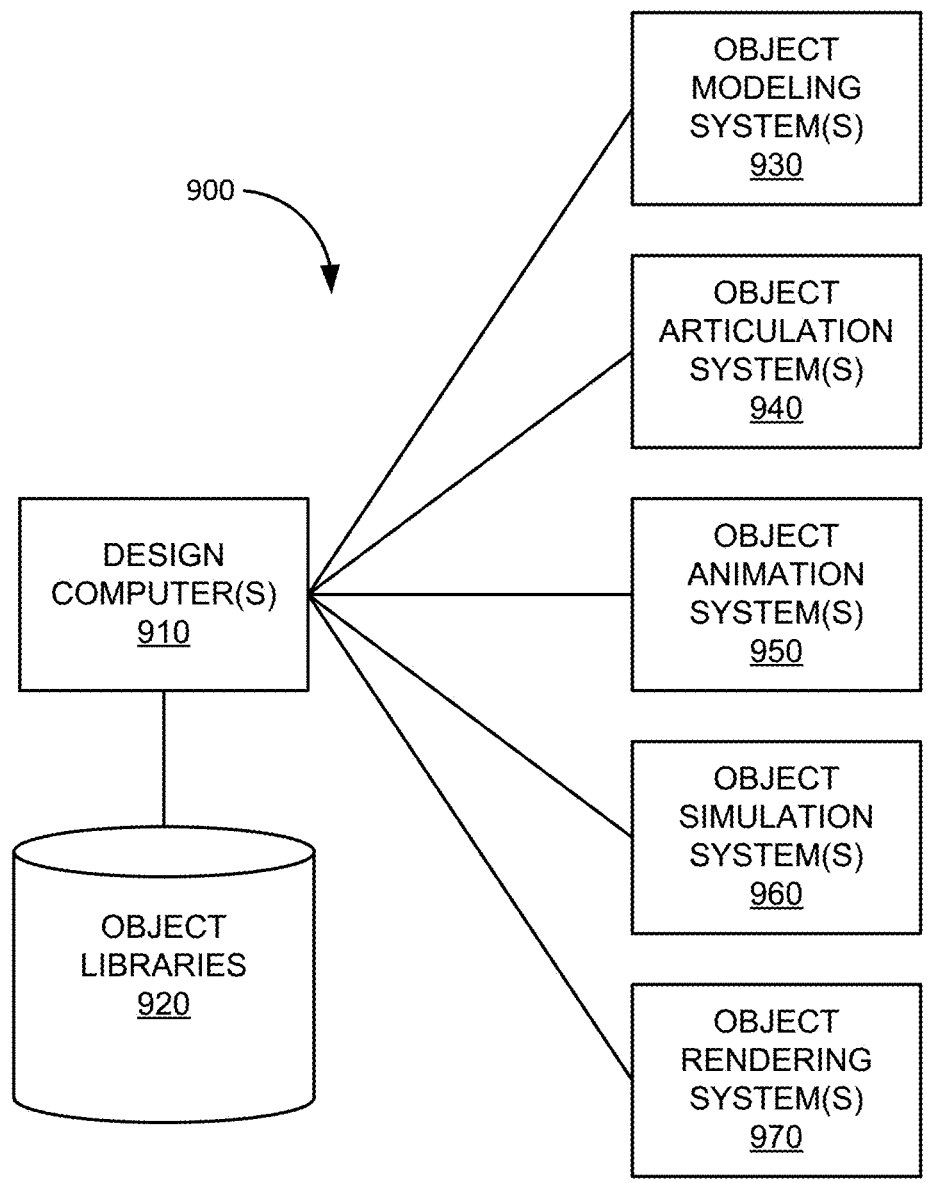
FIG. 9 is a simplified block diagram of system for creating computer graphics imagery (CGI) and computer-aided animation that may implement or incorporate various embodiments.

FIG. 9 is a simplified block diagram of system 900 for creating computer graphics imagery (CGI) and computer-aided animation that may implement or incorporate various embodiments. In this example, system 900 can include one or more design computers 910, object library 920, one or more object modeler systems 930, one or more object articulation systems 940, one or more object animation systems 950, one or more object simulation systems 960, and one or more object rendering systems 980. Any of the systems 930-980 may be invoked by or used directly by a user of the one or more design computers 910 and/or automatically invoked by or used by one or more processes associated with the one or more design computers 910. Any of the elements of system 900 can include hardware and/or software elements configured for specific functions.

The one or more design computers 910 can include hardware and software elements configured for designing CGI and assisting with computer-aided animation. Each of the one or more design computers 910 may be embodied as a single computing device or a set of one or more computing devices. Some examples of computing devices are PCs, laptops, workstations, mainframes, cluster computing system, grid computing systems, cloud computing systems, embedded devices, computer graphics devices, gaming devices and consoles, consumer electronic devices having programmable processors, or the like. The one or more design computers 910 may be used at various stages of a production process (e.g., pre-production, designing, creating, editing, simulating, animating, rendering, post-production, etc.) to produce images, image sequences, motion pictures, video, audio, or associated effects related to CGI and animation.

In one example, a user of the one or more design computers 910 acting as a modeler may employ one or more systems or tools to design, create, or modify objects within a computer-generated scene. The modeler may use modeling software to sculpt and refine a 3D model to fit predefined aesthetic needs of one or more character designers. The modeler may design and maintain a modeling topology conducive to a storyboarded range of deformations. In another example, a user of the one or more design computers 910 acting as an articulator may employ one or more systems or tools to design, create, or modify controls or animation variables (avars) of models. In general, rigging is a process of giving an object, such as a character model, controls for movement, therein "articulating" its ranges of motion. The articulator may work closely with one or more animators in rig building to provide and refine an articulation of the full range of expressions and body movement needed to support a character's acting range in an animation. In a further example, a user of design computer 910 acting as an animator may employ one or more systems or tools to specify motion and position of one or more objects over time to produce an animation.

Object library 920 can include elements configured for storing and accessing information related to objects used by the one or more design computers 910 during the various stages of a production process to produce CGI and animation. Some examples of object library 920 can include a file, a database, or other storage devices and mechanisms. Object library 920 may be locally accessible to the one or more design computers 910 or hosted by one or more external computer systems.

Some examples of information stored in object library 920 can include an object itself, metadata, object geometry, object topology, rigging, control data, animation data, animation cues, simulation data, texture data, lighting data, shader code, or the like. An object stored in object library 920 can include any entity that has an n-dimensional (e.g., 2D or 3D) surface geometry. The shape of the object can include a set of points or locations in space (e.g., object space) that make up the object's surface. Topology of an object can include the connectivity of the surface of the object (e.g., the genus or number of holes in an object) or the vertex/edge/face connectivity of an object.

The one or more object modeling systems 930 can include hardware and/or software elements configured for modeling one or more objects. Modeling can include the creating, sculpting, and editing of an object. In various embodiments, the one or more object modeling systems 930 may be configured to generated a model to include a description of the shape of an object. The one or more object modeling systems 930 can be configured to facilitate the creation and/or editing of features, such as non-uniform rational B-splines or NURBS, polygons and subdivision surfaces (or SubDivs), that may be used to describe the shape of an object. In general, polygons are a widely used model medium due to their relative stability and functionality. Polygons can also act as the bridge between NURBS and SubDivs. NURBS are used mainly for their ready-smooth appearance and generally respond well to deformations. SubDivs are a combination of both NURBS and polygons representing a smooth surface via the specification of a coarser piecewise linear polygon mesh. A single object may have several different models that describe its shape.

The one or more object modeling systems 930 may further generate model data (e.g., 2D and 3D model data) for use by other elements of system 900 or that can be stored in object library 920. The one or more object modeling systems 930 may be configured to allow a user to associate additional information, metadata, color, lighting, rigging, controls, or the like, with all or a portion of the generated model data.

The one or more object articulation systems 940 can include hardware and/or software elements configured to articulating one or more computer-generated objects. Articulation can include the building or creation of rigs, the rigging of an object, and the editing of rigging. In various embodiments, the one or more articulation systems 940 can be configured to enable the specification of rigging for an object, such as for internal skeletal structures or eternal features, and to define how input motion deforms the object. One technique is called "skeletal animation," in which a character can be represented in at least two parts: a surface representation used to draw the character (called the skin) and a hierarchical set of bones used for animation (called the skeleton).

The one or more object articulation systems 940 may further generate articulation data (e.g., data associated with controls or animations variables) for use by other elements of system 900 or that can be stored in object library 920. The one or more object articulation systems 940 may be configured to allow a user to associate additional information, metadata, color, lighting, rigging, controls, or the like, with all or a portion of the generated articulation data.

The one or more object animation systems 950 can include hardware and/or software elements configured for animating one or more computer-generated objects. Animation can include the specification of motion and position of an object over time. The one or more object animation systems 950 may be invoked by or used directly by a user of the one or more design computers 910 and/or automatically invoked by or used by one or more processes associated with the one or more design computers 910.

In various embodiments, the one or more animation systems 950 may be configured to enable users to manipulate controls or animation variables or utilized character rigging to specify one or more key frames of animation sequence. The one or more animation systems 950 generate intermediary frames based on the one or more key frames. In some embodiments, the one or more animation systems 950 may be configured to enable users to specify animation cues, paths, or the like according to one or more predefined sequences. The one or more animation systems 950 generate frames of the animation based on the animation cues or paths. In further embodiments, the one or more animation systems 950 may be configured to enable users to define animations using one or more animation languages, morphs, deformations, or the like.

The one or more object animations systems 950 may further generate animation data (e.g., inputs associated with controls or animations variables) for use by other elements of system 900 or that can be stored in object library 920. The one or more object animations systems 950 may be configured to allow a user to associate additional information, metadata, color, lighting, rigging, controls, or the like, with all or a portion of the generated animation data.

The one or more object simulation systems 960 can include hardware and/or software elements configured for simulating one or more computer-generated objects. Simulation can include determining motion and position of an object over time in response to one or more simulated forces or conditions. The one or more object simulation systems 960 may be invoked by or used directly by a user of the one or more design computers 910 and/or automatically invoked by or used by one or more processes associated with the one or more design computers 910.

In various embodiments, the one or more object simulation systems 960 may be configured to enables users to create, define, or edit simulation engines, such as a physics engine or physics processing unit (PPU/GPGPU) using one or more physically-based numerical techniques. In general, a physics engine can include a computer program that simulates one or more physics models (e.g., a Newtonian physics model), using variables such as mass, velocity, friction, wind resistance, or the like. The physics engine may simulate and predict effects under different conditions that would approximate what happens to an object according to the physics model. The one or more object simulation systems 960 may be used to simulate the behavior of objects, such as hair, fur, and cloth, in response to a physics model and/or animation of one or more characters and objects within a computer-generated scene.

The one or more object simulation systems 960 may further generate simulation data (e.g., motion and position of an object over time) for use by other elements of system 100 or that can be stored in object library 920. The generated simulation data may be combined with or used in addition to animation data generated by the one or more object animation systems 950. The one or more object simulation systems 960 may be configured to allow a user to associate additional information, metadata, color, lighting, rigging, controls, or the like, with all or a portion of the generated simulation data.

The one or more object rendering systems 980 can include hardware and/or software element configured for "rendering" or generating one or more images of one or more computer-generated objects. "Rendering" can include generating an image from a model based on information such as geometry, viewpoint, texture, lighting, and shading information. The one or more object rendering systems 980 may be invoked by or used directly by a user of the one or more design computers 910 and/or automatically invoked by or used by one or more processes associated with the one or more design computers 910. One example of a software program embodied as the one or more object rendering systems 980 can include PhotoRealistic RenderMan, or PRMan, produced by Pixar Animations Studios of Emeryville, Calif.

In various embodiments, the one or more object rendering systems 980 can be configured to render one or more objects to produce one or more computer-generated images or a set of images over time that provide an animation. The one or more object rendering systems 980 may generate digital images or raster graphics images.

In various embodiments, a rendered image can be understood in terms of a number of visible features. Some examples of visible features that may be considered by the one or more object rendering systems 980 may include shading (e.g., techniques relating to how the color and brightness of a surface varies with lighting), texture-mapping (e.g., techniques relating to applying detail information to surfaces or objects using maps), bump-mapping (e.g., techniques relating to simulating small-scale bumpiness on surfaces), fogging/participating medium (e.g., techniques relating to how light dims when passing through non-clear atmosphere or air) shadows (e.g., techniques relating to effects of obstructing light), soft shadows (e.g., techniques relating to varying darkness caused by partially obscured light sources), reflection (e.g., techniques relating to mirror-like or highly glossy reflection), transparency or opacity (e.g., techniques relating to sharp transmissions of light through solid objects), translucency (e.g., techniques relating to highly scattered transmissions of light through solid objects), refraction (e.g., techniques relating to bending of light associated with transparency), diffraction (e.g., techniques relating to bending, spreading and interference of light passing by an object or aperture that disrupts the ray), indirect illumination (e.g., techniques relating to surfaces illuminated by light reflected off other surfaces, rather than directly from a light source, also known as global illumination), caustics (e.g., a form of indirect illumination with techniques relating to reflections of light off a shiny object, or focusing of light through a transparent object, to produce bright highlight rays on another object), depth of field (e.g., techniques relating to how objects appear blurry or out of focus when too far in front of or behind the object in focus), motion blur (e.g., techniques relating to how objects appear blurry due to high-speed motion, or the motion of the camera), non-photorealistic rendering (e.g., techniques relating to rendering of scenes in an artistic style, intended to look like a painting or drawing), or the like.

The one or more object rendering systems 980 may further render images (e.g., motion and position of an object over time) for use by other elements of system 900 or that can be stored in object library 920. The one or more object rendering systems 980 may be configured to allow a user to associate additional information or metadata with all or a portion of the rendered image.

Figure 10:
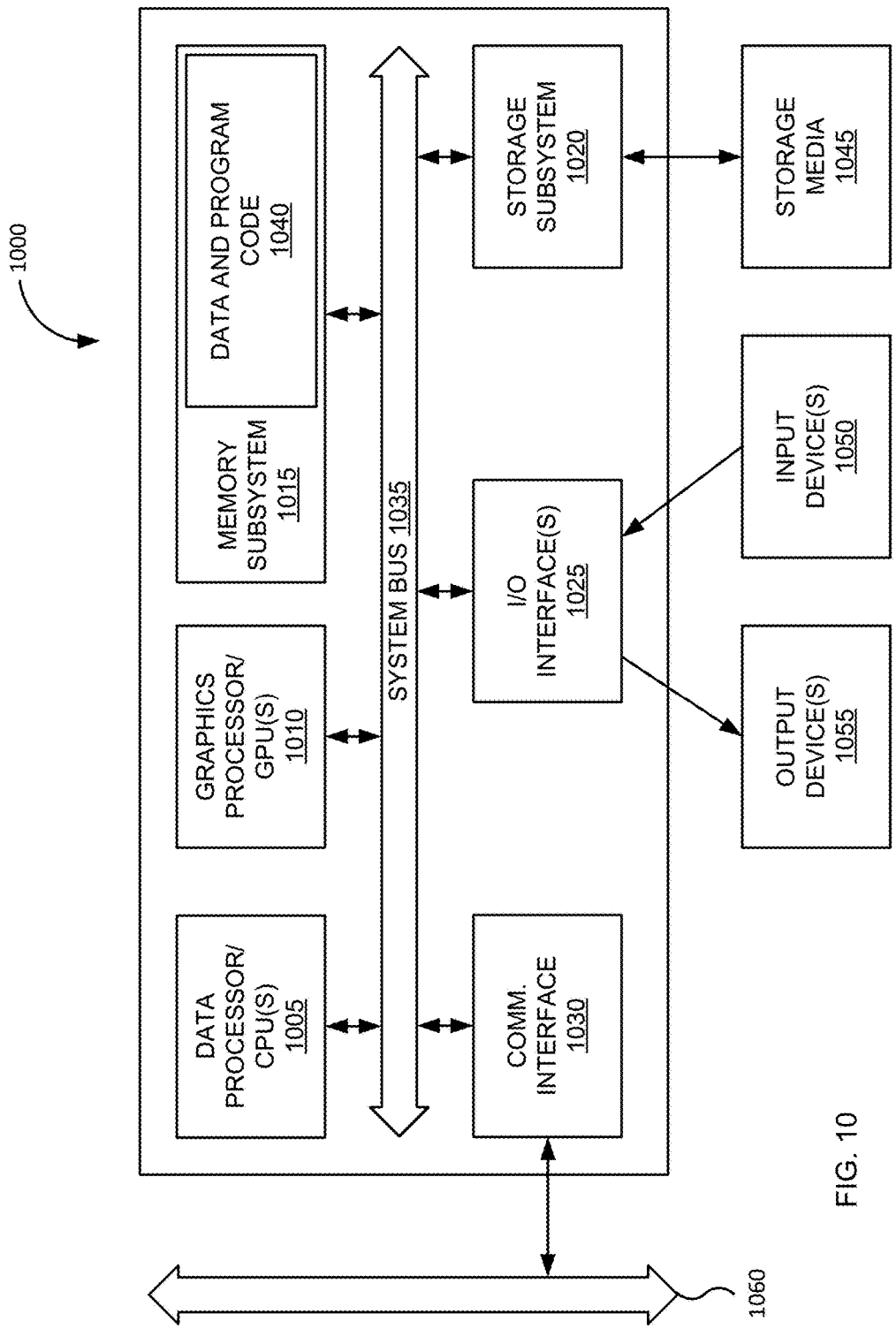
FIG. 10 is a block diagram of computer system for implementing various embodiments in accordance with the disclosure.

FIG. 10 is a block diagram of computer system 1000. FIG. 10 is merely illustrative. In some embodiments, a computer system includes a single computer apparatus, where the subsystems can be the components of the computer apparatus. In other embodiments, a computer system can include multiple computer apparatuses, each being a subsystem, with internal components. Computer system 1000 and any of its components or subsystems can include hardware and/or software elements configured for performing methods described herein.

Computer system 1000 may include familiar computer components, such as one or more one or more data processors or central processing units (CPUs) 1005, one or more graphics processors or graphical processing units (GPUs) 1010, memory subsystem 1015, storage subsystem 1020, one or more input/output (I/O) interfaces 1025, communications interface 1030, or the like. Computer system 1000 can include system bus 1035 interconnecting the above components and providing functionality, such connectivity and inter-device communication.

The one or more data processors or central processing units (CPUs) 1005 can execute logic or program code or for providing application-specific functionality. Some examples of CPU(s) 1005 can include one or more microprocessors (e.g., single core and multi-core) or micro-controllers, one or more field-gate programmable arrays (FPGAs), and application-specific integrated circuits (ASICs). As used herein, a processor includes a multi-core processor on a same integrated chip, or multiple processing units on a single circuit board or networked.

The one or more graphics processor or graphical processing units (GPUs) 1010 can execute logic or program code associated with graphics or for providing graphics-specific functionality. GPUs 1010 may include any conventional graphics processing unit, such as those provided by conventional video cards. In various embodiments, GPUs 1010 may include one or more vector or parallel processing units. These GPUs may be user programmable, and include hardware elements for encoding/decoding specific types of data (e.g., video data) or for accelerating 2D or 3D drawing operations, texturing operations, shading operations, or the like. The one or more graphics processors or graphical processing units (GPUs) 1010 may include any number of registers, logic units, arithmetic units, caches, memory interfaces, or the like.

Memory subsystem 1015 can store information, e.g., using machine-readable articles, information storage devices, or computer-readable storage media. Some examples can include random access memories (RAM), read-only-memories (ROMS), volatile memories, non-volatile memories, and other semiconductor memories. Memory subsystem 1015 can include data and program code 1040.

Storage subsystem 1020 can also store information using machine-readable articles, information storage devices, or computer-readable storage media. Storage subsystem 1020 may store information using storage media 1045. Some examples of storage media 1045 used by storage subsystem 1020 can include floppy disks, hard disks, optical storage media such as CD-ROMs, DVDs and bar codes, removable storage devices, networked storage devices, or the like. In some embodiments, all or part of data and program code 1040 may be stored using storage subsystem 1020.

The one or more input/output (I/O) interfaces 1025 can perform I/O operations. One or more input devices 1050 and/or one or more output devices 1055 may be communicatively coupled to the one or more I/O interfaces 1025. The one or more input devices 1050 can receive information from one or more sources for computer system 1000. Some examples of the one or more input devices 1050 may include a computer mouse, a trackball, a track pad, a joystick, a wireless remote, a drawing tablet, a voice command system, an eye tracking system, external storage systems, a monitor appropriately configured as a touch screen, a communications interface appropriately configured as a transceiver, or the like. In various embodiments, the one or more input devices 1050 may allow a user of computer system 1000 to interact with one or more non-graphical or graphical user interfaces to enter a comment, select objects, icons, text, user interface widgets, or other user interface elements that appear on a monitor/display device via a command, a click of a button, or the like.

The one or more output devices 1055 can output information to one or more destinations for computer system 1000. Some examples of the one or more output devices 1055 can include a printer, a fax, a feedback device for a mouse or joystick, external storage systems, a monitor or other display device, a communications interface appropriately configured as a transceiver, or the like. The one or more output devices 1055 may allow a user of computer system 1000 to view objects, icons, text, user interface widgets, or other user interface elements. A display device or monitor may be used with computer system 1000 and can include hardware and/or software elements configured for displaying information.

Communications interface 1030 can perform communications operations, including sending and receiving data. Some examples of communications interface 1030 may include a network communications interface (e.g. Ethernet, Wi-Fi, etc.). For example, communications interface 1030 may be coupled to communications network/external bus 1060, such as a computer network, a USB hub, or the like. A computer system can include a plurality of the same components or subsystems, e.g., connected together by communications interface 1030 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Computer system 1000 may also include one or more applications (e.g., software components or functions) to be executed by a processor to execute, perform, or otherwise implement techniques disclosed herein. These applications may be embodied as data and program code 1040. Additionally, computer programs, executable computer code, human-readable source code, shader code, rendering engines, or the like, and data, such as image files, models including geometrical descriptions of objects, ordered geometric descriptions of objects, procedural descriptions of models, scene descriptor files, or the like, may be stored in memory subsystem 1015 and/or storage subsystem 1020.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method for reconstructing a three-dimensional (3D) model of teeth of an object from one or more images of the object, the method being performed by a computer system and comprising:
   receiving, by the computer system, sample data of teeth rows of different sample subjects;
   receiving, by the computer system, tooth templates comprising individual template teeth;
   mapping, by the computer system, individual teeth in the teeth rows of the different sample subjects to the individual template teeth;
   for each of the individual template teeth, obtaining, by the computer system, a teeth statistical model, the statistical model encoding a deviation in shape and pose for each of the individual template teeth, wherein the teeth statistical model includes information regarding a rigid transformation and an anisotropic scaling factor for the teeth rows, the anisotropic scaling factor comprising different properties depending on a direction of measurement for the teeth rows;
   training, by the computer system, each teeth statistical model using the sample data of the teeth rows of the different sample subjects based on the mapping between the individual teeth in the teeth rows of the different sample subjects and the individual template teeth, wherein the training comprises: evaluating the teeth statistics model to provide an instance of a teeth row that represents either an upper or a lower teeth for a sample subject;
   acquiring, by the computer system, teeth information from the one or more images of the object; and
   reconstructing, by the computer system, a 3D model of teeth of the object by fitting parameters of the trained teeth statistical model to the teeth information acquired from the one or more images of the object.

2. The method of claim 1, wherein the teeth statistical model encodes an average shape of the tooth, an average pose of the tooth, deviation in shape and pose for the tooth across the different sample subjects, and placement of the tooth in a generic teeth row.

3. The method of claim 1, wherein the received sample data of the teeth rows of the different sample subjects are 3D scans of a mouth region of the different sample subjects.

4. The method of claim 1, wherein training the teeth statistical model comprises
   performing a principal component analysis to determine a variation in shape for each tooth template.

5. The method of claim 1, wherein mapping individual teeth in the teeth rows of the different sample subject to the individual template teeth includes receiving an indication of a segmentation contour for the individual teeth, the segmentation contour indicating separation of each of the individual teeth and separation of the teeth and a gum region.

6. The method of claim 5, wherein the indication further includes marks representing one or more land marks on the individual template teeth.

7. The method of claim 5, further comprising computing segmentation contour for each tooth based on the received indication.

8. The method of claim 1, wherein a teeth statistical model is obtained for each type of teeth in the teeth row.

9. A system for reconstructing a three-dimensional (3D) model of teeth of an object from one or more images of the object, wherein the system comprises one or more processors configured to execute machine-readable instructions such that when the machine-readable instructions are executed by the one or more processors, the one or more processors are caused to perform:
   receiving sample data of teeth rows of different sample subjects;
   receiving tooth templates comprising individual template teeth;
   mapping individual teeth in the teeth rows of the different sample subject to the individual template teeth;
   for each of the individual template teeth, obtaining a teeth statistical model, the statistical model encoding a deviation in shape and pose for each of the individual template teeth, wherein the teeth statistical model includes information regarding a rigid transformation and an anisotropic scaling factor for the teeth rows, the anisotropic scaling factor comprising different properties depending on a direction of measurement for the teeth rows;

training each teeth statistical model using the sample data of the teeth rows of the different sample subjects based on the mapping between the individual teeth in the teeth rows of the different sample subjects and the individual template teeth, wherein the training comprises: evaluating the teeth statistics model to provide an instance of a teeth row that represents either upper or lower teeth for a sample subject;

acquiring teeth information from the one or more images of the object; and reconstructing a 3D model of teeth of the object by fitting parameters of the trained statistical model to the teeth information acquired from the one or more images of the object.

10. The system of claim 9, wherein the teeth statistical model encodes an average shape of the tooth, an average pose of the tooth, deviation in shape and pose for the tooth across the subjects, and placement of the tooth in a generic teeth row.

11. The system of claim 9, wherein the received sample data of the teeth rows of the different sample subjects are 3D scans of a mouth region of the different sample subjects.

12. The system of claim 9, wherein training the teeth statistical model comprises
performing a principal component analysis to determine a variation in shape for each tooth template.

13. The system of claim 9, wherein mapping individual teeth in the teeth rows of the different sample subject to the individual template teeth includes receiving an indication of a segmentation contour for the individual teeth, the segmentation contour indicating separation of each of the individual teeth and separation of the teeth and a gum region.

14. The system of claim 13, wherein the indication further includes marks representing one or more land marks on the individual template teeth.

15. The system of claim 13, further comprising computing segmentation contour for each tooth based on the received indication.

16. The system of claim 9, wherein a teeth statistical model is obtained for each type of teeth in the teeth row.

* * * * *